(12) United States Patent
Yodfat et al.

(10) Patent No.: US 8,439,897 B2
(45) Date of Patent: May 14, 2013

(54) ASSESSING RESIDUAL INSULIN TIME

(75) Inventors: Ofer Yodfat, Maccabim-Reut (IL); Gali Shapira, Haifa (IL)

(73) Assignee: Medingo Ltd., Yoqneam Illit, IL (US)

( * ) Notice: Subject to any disclaimer, the term of this patent is extended or adjusted under 35 U.S.C. 154(b) by 207 days.

(21) Appl. No.: 12/742,173

(22) PCT Filed: Nov. 4, 2008

(86) PCT No.: PCT/IL2008/001444
§ 371 (c)(1),
(2), (4) Date: May 10, 2010

(87) PCT Pub. No.: WO2009/060433
PCT Pub. Date: May 14, 2009

(65) Prior Publication Data
US 2010/0256458 A1    Oct. 7, 2010

Related U.S. Application Data

(60) Provisional application No. 61/002,530, filed on Nov. 9, 2007.

(51) Int. Cl.
*A61K 9/22* (2006.01)
(52) U.S. Cl.
USPC ...................................................... 604/891.1
(58) Field of Classification Search .............. 604/65–66, 604/504, 890.1, 891.1
See application file for complete search history.

(56) References Cited

U.S. PATENT DOCUMENTS

| | | | |
|---|---|---|---|
| 7,291,107 B2 * | 11/2007 | Hellwig et al. | 600/365 |
| 7,806,886 B2 * | 10/2010 | Kanderian et al. | 604/504 |
| 2006/0047192 A1 * | 3/2006 | Hellwig et al. | 600/365 |
| 2006/0224109 A1 * | 10/2006 | Steil et al. | 604/66 |
| 2007/0173761 A1 * | 7/2007 | Kanderian et al. | 604/131 |
| 2007/0191702 A1 | 8/2007 | Yodfat et al. | |
| 2008/0071580 A1 * | 3/2008 | Marcus et al. | 705/3 |

(Continued)

FOREIGN PATENT DOCUMENTS

DE 102 41 550 A1    4/2004
EP 1 281 351 A      2/2003

OTHER PUBLICATIONS

The Diabetes Control and Complications Trial (DCCT) Research Group, "The Effect of Intensive Treatment of Diabetes on the Development and Progression of Long-Term Complications in Insulin-Dependent Diabetes Mellitus", *N. Engl J Med* 329: 977-986 (1993).

(Continued)

*Primary Examiner* — Nicholas Lucchesi
*Assistant Examiner* — Diva K Chander
(74) *Attorney, Agent, or Firm* — Mintz Levin Cohn Ferris Glovsky and Popeo, P.C.

(57) ABSTRACT

Methods, systems and devices for assessing residual insulin time of a patient are provided. In one embodiment, the method and the device can be implemented by receiving a confirmation that an insulin dose has been administered to the patient; repetitively receiving a value corresponding to the patient's blood glucose level; identifying at least two consecutively received values based on a predetermined criteria; and, selecting the residual insulin time corresponding to a time period between the confirmation that the insulin dose has been administered and a time corresponding to the identification of the at least two consecutively received values.

22 Claims, 15 Drawing Sheets

| Dose Given [IU] | Units left to work after: | | | | |
|---|---|---|---|---|---|
| | 1 Hr | 2 Hr | 3 Hr | 4 Hr | 5 Hr |
| 1 | 0.8 | 0.6 | 0.4 | 0.2 | 0 |
| 2 | 1.6 | 1.2 | 0.8 | 0.4 | 0 |
| 3 | 2.4 | 1.8 | 1.2 | 0.6 | 0 |
| 4 | 3.2 | 2.4 | 1.6 | 0.8 | 0 |
| 5 | 4.0 | 3.0 | 2.0 | 1.0 | 0 |
| 6 | 4.8 | 3.6 | 2.4 | 1.2 | 0 |
| 7 | 5.6 | 4.2 | 2.8 | 1.4 | 0 |
| 8 | 6.4 | 4.8 | 3.2 | 1.6 | 0 |
| 9 | 7.2 | 5.4 | 3.6 | 1.8 | 0 |
| 10 | 8.0 | 6.0 | 4.0 | 2.0 | 0 |

U.S. PATENT DOCUMENTS

2008/0172031 A1* 7/2008 Blomquist ............... 604/500
2008/0215035 A1 9/2008 Yodfat et al.
2009/0018406 A1 1/2009 Yodfat et al.

OTHER PUBLICATIONS

UK Prospective Diabetes Study (UKPDS) Group, Intensive Blood-Glucose Control with Sulphonylureas or Insulin Compared with Conventional Treatment and Risk of Complications in Patients with Type 2 Diabetes (UKPDS 33), The Lancet 352: 837-853 (1998).

UK Prospective Diabetes Study (UKPDS) Group, "Tight Blood Pressure Control and Risk of Macrovascular and Microvascular in Type 2 Diabetes: UKPDS 38", BMJ 317, (7160): 703-13 (1998).

The Diabetes Control and Complications Trial/Epidemiology of Diabetes Interventions and Complications (DCCT/EDIC) Study Research Group, "Intensive Diabetes Treatment and Cardiovascular Disease in Patients with Type 1 Diabetes", N. Engl J Med 353 (25): 2643-53 (2005).

J. Walsh R. Roberts, C.B. Varma and T. Bailey, "Using Insulin, Everything You Need for Success with Insulin" *Torrey Pines Press*, 2003.

International Search Report and Written Opinion for PCT Application No. PCT/IL2008/001444 date of mailing Apr. 22, 2009.

* cited by examiner

| Dose Given [IU] | Units left to work after: | | | | |
|---|---|---|---|---|---|
| | 1 Hr | 2 Hr | 3 Hr | 4 Hr | 5 Hr |
| 1 | 0.8 | 0.6 | 0.4 | 0.2 | 0 |
| 2 | 1.6 | 1.2 | 0.8 | 0.4 | 0 |
| 3 | 2.4 | 1.8 | 1.2 | 0.6 | 0 |
| 4 | 3.2 | 2.4 | 1.6 | 0.8 | 0 |
| 5 | 4.0 | 3.0 | 2.0 | 1.0 | 0 |
| 6 | 4.8 | 3.6 | 2.4 | 1.2 | 0 |
| 7 | 5.6 | 4.2 | 2.8 | 1.4 | 0 |
| 8 | 6.4 | 4.8 | 3.2 | 1.6 | 0 |
| 9 | 7.2 | 5.4 | 3.6 | 1.8 | 0 |
| 10 | 8.0 | 6.0 | 4.0 | 2.0 | 0 |

*Fig. 1*

| Classification | GI range | Examples |
|---|---|---|
| Low GI | 55 or less | most fruit and vegetables (but not potato), oats, buckwheat, whole barley, All-bran |
| Medium GI | 56 – 69 | sucrose, basmati rice |
| High GI | 70 or more | cornflakes, baked potato, jasmine rice, white bread, white rice, Mars bar |

*Fig. 2*

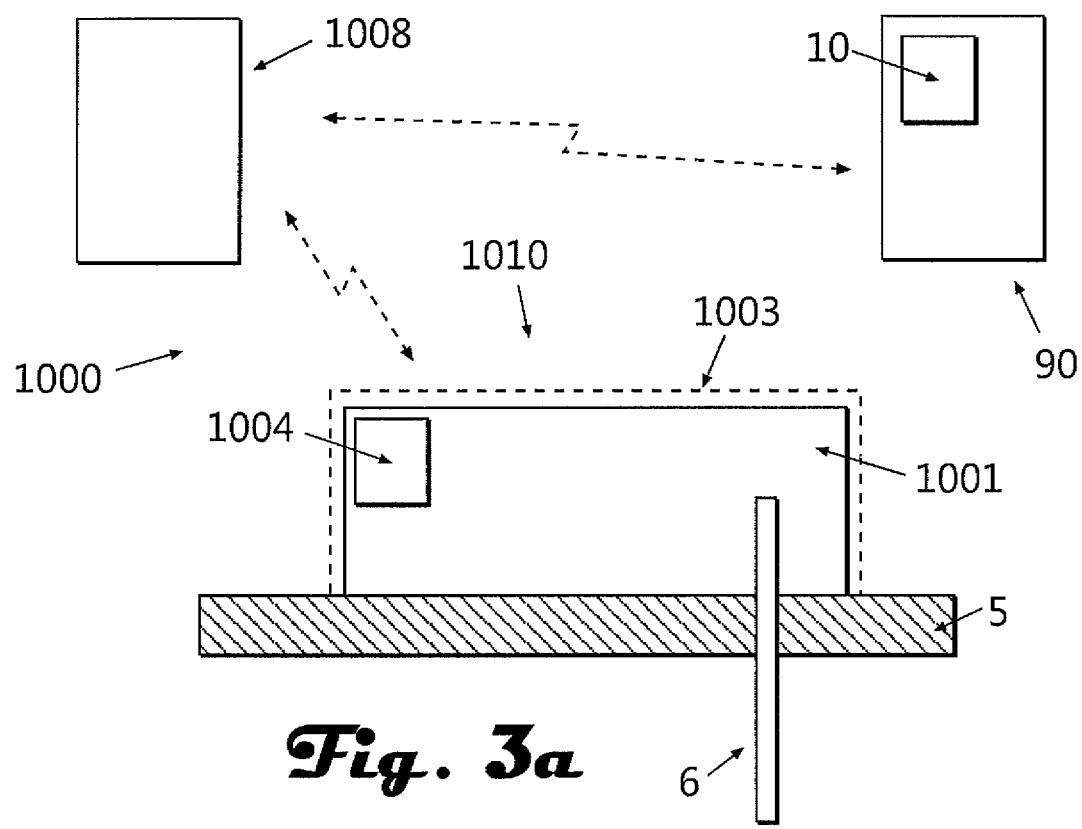
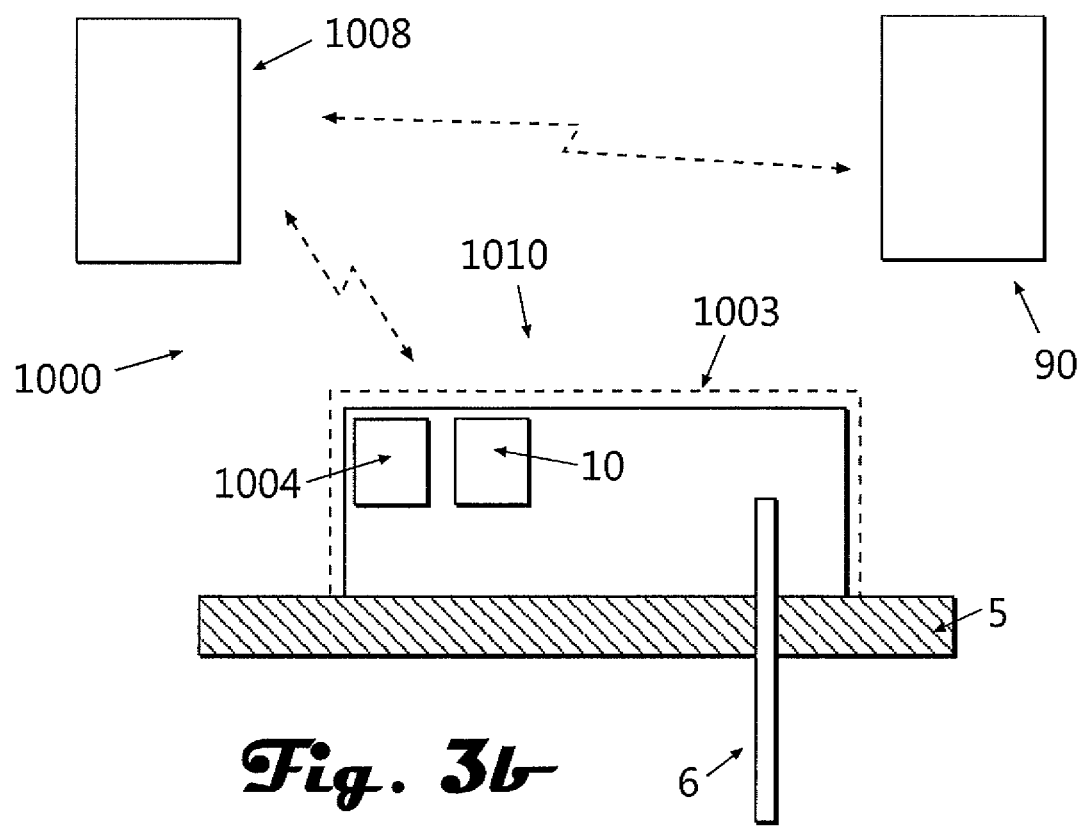

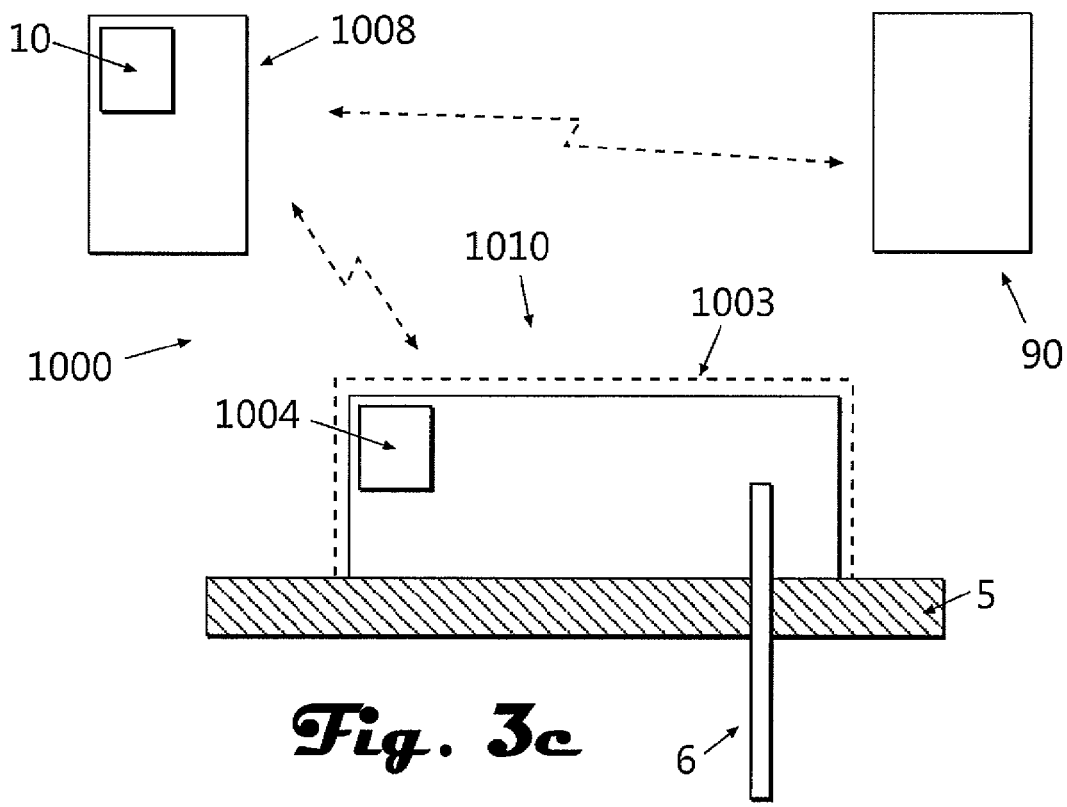
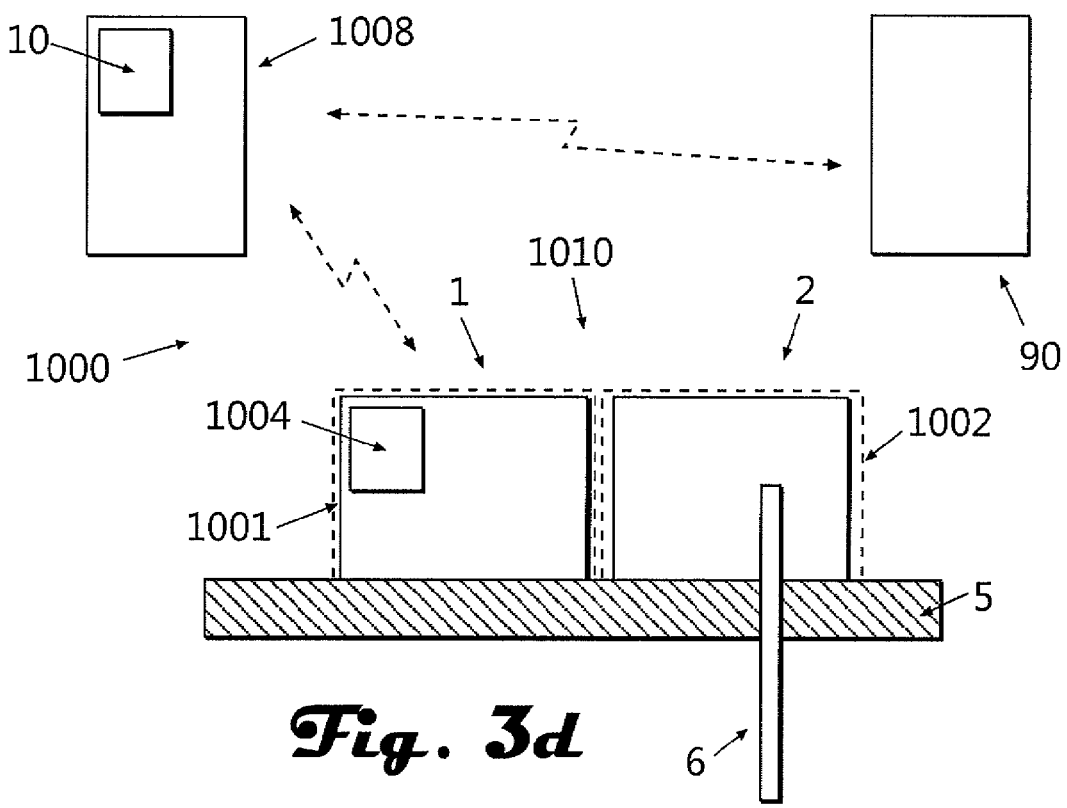

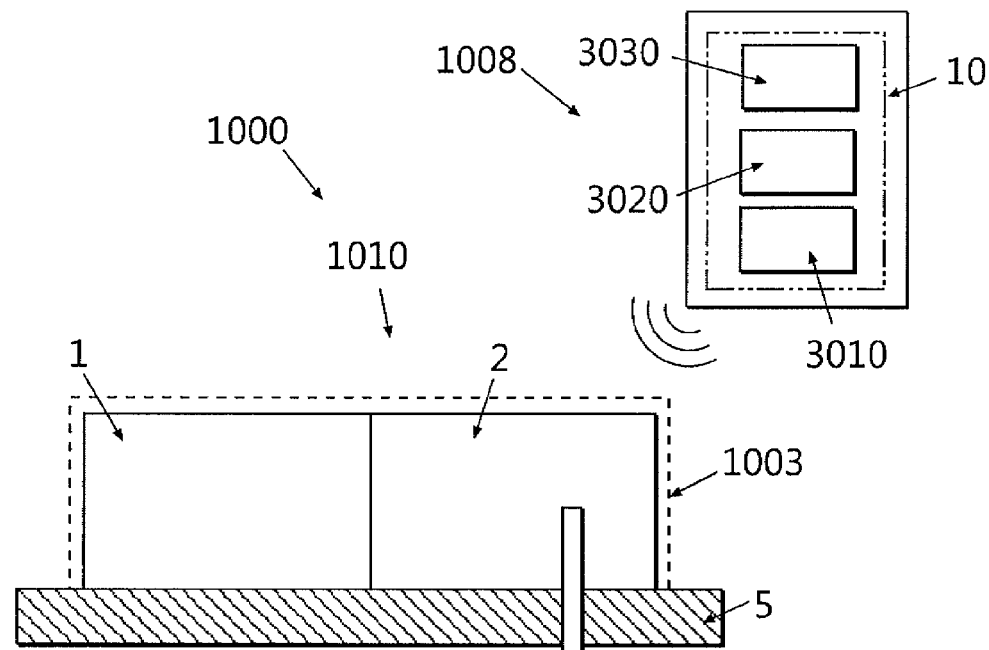
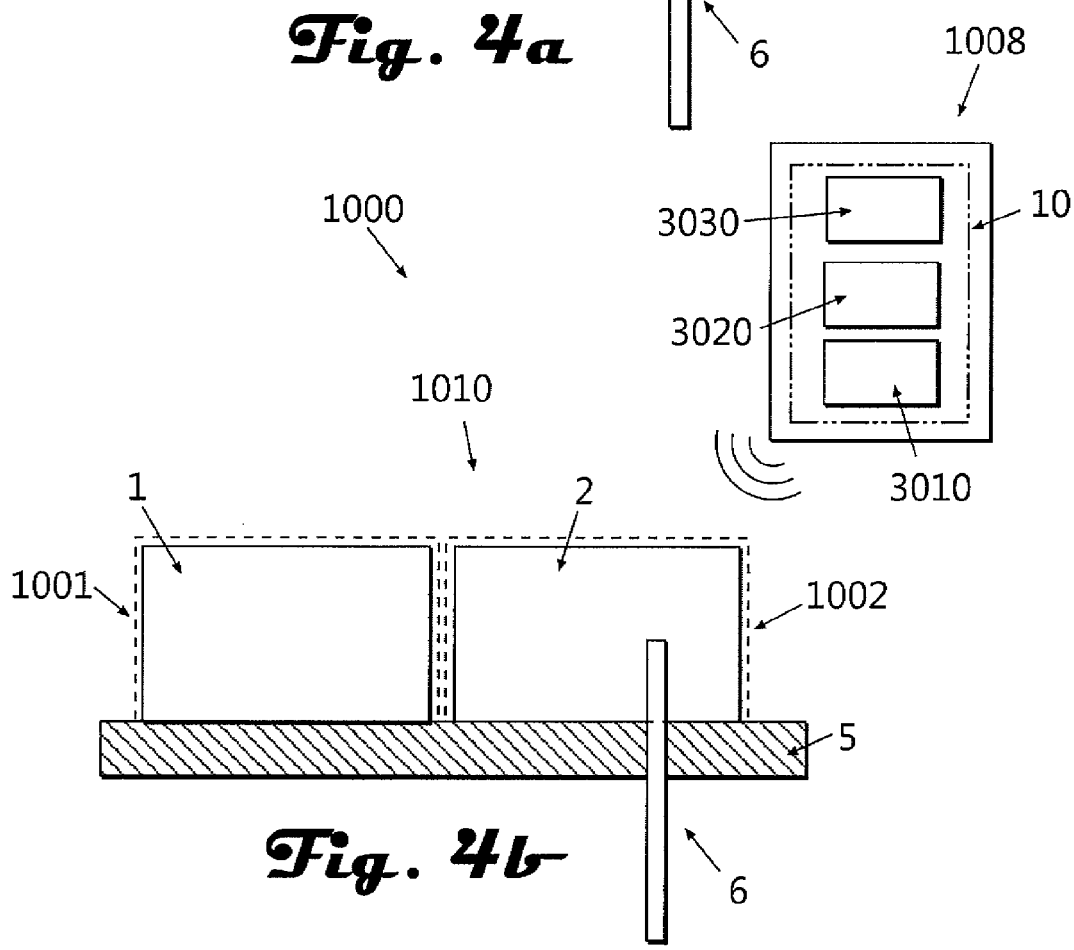

ASSESSING RESIDUAL INSULIN TIME

CROSS-REFERENCE TO RELATED APPLICATIONS

The present application is a 35 U.S.C. §371 national stage entry of PCT/IL2008/001444, which has an international filing date of 4 Nov. 2008 and claims priority to U.S. Provisional Patent Application No. 61/002,530, filed on 9 Nov. 2007. The present application incorporates herein by reference the disclosure of each of the above-referenced applications in its entirety.

FIELD

Methods, systems and devices for sustained medical infusion of therapeutic fluids to patients are described. Some embodiments relate to portable infusion devices and to a method for infusion that includes administering a therapeutic fluid to the patient after assessing a diabetes related parameter of the patient. Some embodiments relate to an insulin-dispensing device configured to sense a glucose level in the blood of the patient and to a method for infusing insulin after assessing diabetes related parameters.

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin according to the blood glucose levels, maintaining near constant glucose levels in the body.

Much of the burden of the disease to the user and to health care resources is due to the long-term tissue complications, which affect both the small blood vessels (microangiopathy, causing eye, kidney and nerve damage) and the large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbA1c). [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining normoglycemia by frequent glucose measurements and adjustment of insulin delivery accordingly can be of utmost importance.

Insulin pumps can deliver rapid acting insulin (i.e. Lispro, Aspart, etc.) 24 hours a day through a catheter placed under the skin. Rapid acting insulin effect begins in about 10 minutes, peaks at one to one and a half hours and ends in about two to six hours after the administration.

A simple rule can be applied to calculate the duration of insulin activity. It is often stated that 20% of a dose can be used each hour after bolus administration, so that after 5 hours there is no active insulin remaining in the body. FIG. 1 shows the insulin consumption according to the described rule (adapted from Using Insulin © 2003).

One of the major advantages of using insulin pumps is the convenience of insulin bolus administration at any desired time. However, boluses may overlap and it can be useful to know the amount of active insulin that is still "working" (hereinafter "residual insulin" or "RI"). Accumulation of insulin may lead to life-threatening hypoglycemia. This is especially important at bedtime since users are usually unaware of nocturnal hypoglycemia.

Many insulin pumps can apply the abovementioned rule to calculate the residual insulin and subtract the calculated value from current administered bolus. For example, if previously administered bolus was 6 IU, current (e.g., 2 hours after the previous bolus) administered bolus is 5 IU, RI 2 hours after the previously administered bolus is 3.6 IU, the actually delivered bolus should be 1.4 IU (5IU-3.6IU).

Application of the abovementioned rule can lead to over or under dosing due to significant individuality variability of insulin absorption and consumption. The assumption that the complete bolus absorption time (a state with no residual insulin, RI=0, hereinafter referred to as "residual insulin time" or "RI time") is always 5 hours (20%/hour) ignores individual variability, and, as a result, may not be correct.

For example, if the entire bolus dose is absorbed within 3 hours (i.e. RI time is 3 hours), then following the table in FIG. 1 four hours after the bolus can lead to under dosing. If RI time is 6 hours, then following the table in FIG. 1 five hours after the bolus will lead to overdosing. Accurate, user specific assessment of the RI time can, therefore, be important for maintaining normoglycemia.

SUMMARY

Methods, systems and devices for assessing a residual insulin time of a patient are provided. In one embodiment, the method and the device can be implemented by receiving a confirmation that an insulin dose has been administered to the patient; repetitively receiving a value corresponding to the patient's blood glucose level; identifying at least two consecutively received values based on a predetermined criteria; and, selecting the residual insulin time corresponding to a time period between the confirmation that the insulin dose has been administered and a time corresponding to the identification of the at least two consecutively received values. For example, the time corresponding to the identification of the at least two consecutively received values can be the time when the first of the two identified values was received. The time corresponding to the identification of the at least two consecutively received values can also be the time when the second of the two identified values was received. It can also be derived from the times when the first value and the second value were received.

The predetermined criteria can be based on a target blood glucose range. The predetermined criteria can also be based on an initial blood glucose level measured prior to the administration of the insulin dose. The predetermined criteria can also be based on a difference between the at least two consecutively received values. For example, the predetermined criteria can be satisfied if the difference between the at least two consecutively received values is less than 20 mg/dL. The predetermined criteria can also be based on a third consecutively received value corresponding to the patient's blood glucose level. For example, the at least two consecutively received values can be identified if the difference between the third consecutive value and the first consecutive value is less than a predefined threshold.

In one embodiment, the insulin dose can be administered to the patient subsequently to a confirmation that the patient's blood glucose level is within a target blood glucose range. The insulin dose can also be administered to the patient subsequently to a confirmation that the patient's blood glucose level is outside of a target blood glucose range.

The insulin dose can correspond to an amount of carbohydrates planned to be consumed by the patient. The patient can be advised to bring the patient's blood glucose level within a target blood glucose range prior to consuming the planned amount of carbohydrates. The patient can also be advised to abstain from food for an abstention period of time prior to consuming the planned amount of carbohydrates.

In some embodiments, the two consecutive values can be identified only if both consecutive values are within the target blood glucose range. The two consecutive values can also be identified if only one of the two values appears within the target blood glucose range. Similarly, the two consecutive values can be identified if neither one of them appears within the target blood glucose range. In some embodiments, the value corresponding to the patient's blood glucose level can be repetitively received with a predetermined frequency.

In some embodiments, an administration of a correction bolus can be initiated if the two identified consecutively received values are above the target blood glucose range. For example, the initiation of the administration of the correction bolus can be performed by notifying the patient. The initiation of the administration of the correction bolus can also be performed by activating a pump.

The patient can be advised to reassess a CIR value if the deviation between one of the at least two consecutively received values and the patient's blood glucose level measured prior to the insulin administration exceeds a predefined threshold. The patient can also be advised to consume more carbohydrates, if the two identified consecutively received values are below a target blood glucose range.

In another embodiment, a medical device is provided. In some variations, the medical device can implement the method for assessing a residual insulin time. For example, the medical device can comprise a tangible machine-readable storage medium embodying instructions that when performed by one or more processors result in operations comprising: receiving a confirmation that an insulin dose has been administered to the patient; repetitively receiving a value corresponding to the patient's blood glucose level; identifying at least two consecutively received values based on a predetermined criteria; and, selecting the residual insulin time corresponding to a time period between the confirmation that the insulin dose has been administered and a time when the first of the two identified values was received.

The medical device can also comprise a blood glucose monitor. The medical device can comprise a dispensing apparatus. In some embodiments, the medical device can be wirelessly connected to a dispensing apparatus. For example, the dispensing apparatus can comprise a reusable part and a disposable part.

In some embodiments, the medical device can also comprise a blood glucose monitor. In some embodiments, the device can be, wirelessly connected to a dispensing apparatus. For example, the dispensing apparatus can comprise a reusable part and a disposable part.

BRIEF DESCRIPTION OF THE DRAWINGS

FIG. 1 illustrates insulin activity at 1, 2, 3, 4, and 5 hours after Insulin Lispro bolus administration;

FIG. 2 illustrates few examples of recommended foods and their GIs;

FIGS. 3a-d show the device including an insulin dispensing unit and a remote control unit wherein the RITA feature is contained in a glucose measurement device or in the dispensing patch unit;

FIGS. 4a-c show the insulin infusion device including a dispensing unit and a remote control unit that contains the RITA feature;

DETAILED DESCRIPTION

Figure 4C:
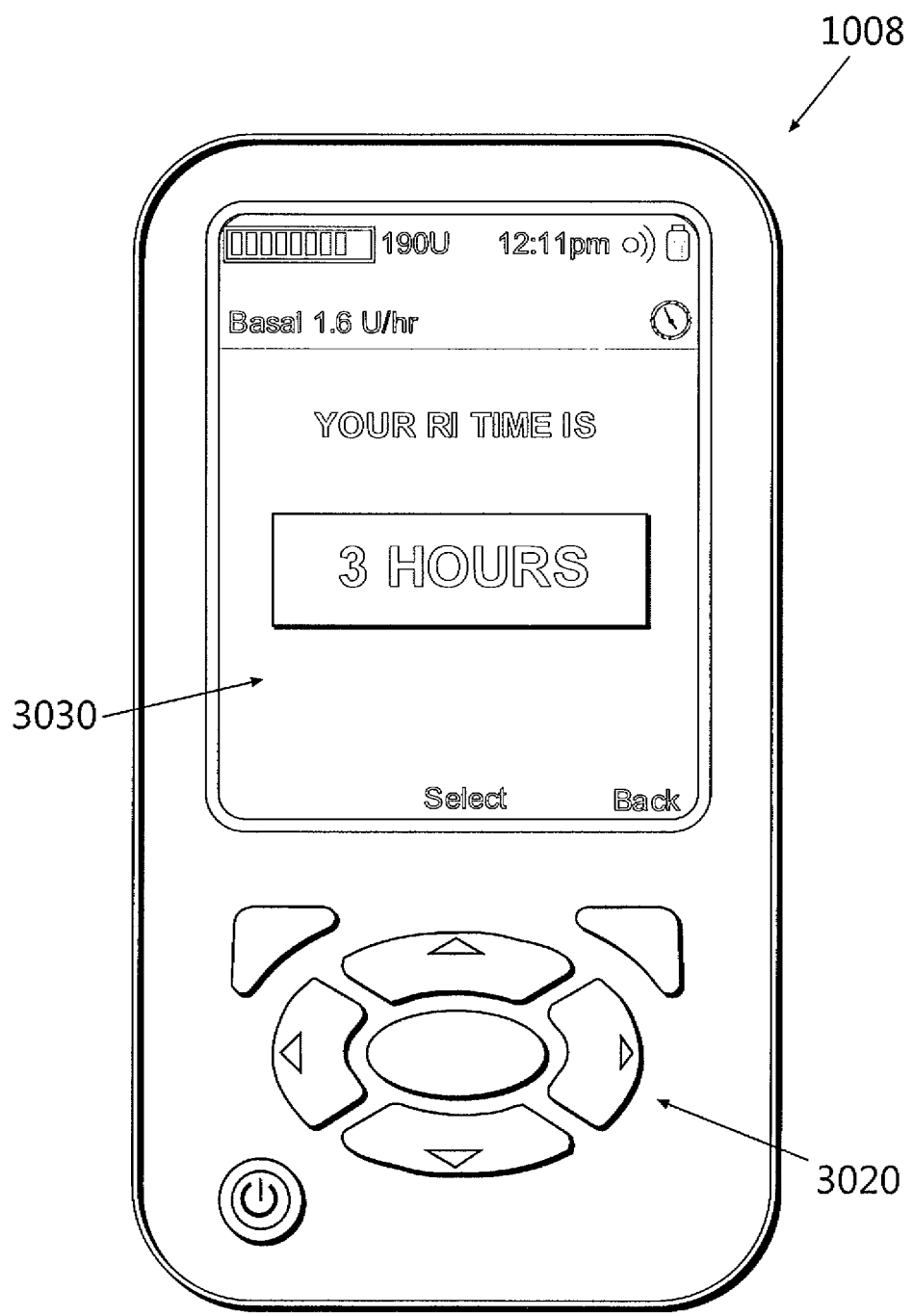

Methods, systems and devices for assessing residual insulin time of a patient are provided. In one embodiment, the method and the device can be implemented by receiving a confirmation that an insulin dose has been administered to the patient; repetitively receiving a value corresponding to the patient's blood glucose level; identifying at least two consecutively received values based on a predetermined criteria; and, selecting the residual insulin time corresponding to a time period between the confirmation that the insulin dose has been administered and a time corresponding to the identification of the at least two consecutively received values.

In one embodiment, the Residual Insulin Time Assessment ("RITA") method can be performed after the patient abstains from food and rests for at least six hours. For example, the RITA method can be performed after a night's sleep, thereby eliminating possible long RI time effect. In some embodiments, the RI time can be assessed when fasting glucose is within the target zone.

The RITA method can use a notification that the patient contemplates to consume a snack containing a known amount of carbohydrates of a high glycemic index (e.g., a marketed bag of pretzels). The glycemic index ("GI") is a ranking system for carbohydrates based on their effects on blood glucose levels in the first two hours. Preferably, the snack should not be a high-fat or high-protein food, because this type of food can take longer to digest and is slower to affect the blood glucose ("BG"). For example, FIG. 2 provides a few examples of recommended foods and their GIs. In some embodiments the blood glucose level can correspond to the concentration of glucose in the blood of the patient. The blood glucose level can also be derived from the measurements made in the subcutaneous tissue or interstitial fluid.

According to the RITA method, the patient can be administered a normal insulin bolus (as opposed to the extended bolus). The bolus amount can be selected according to the contemplated carbohydrate intake. The administered bolus can also be calculated by using the carbohydrate load divided by the CIR-values (i.e., bolus=Carb/CIR values).

According to the RITA method, the patient can provide a notification that the contemplated snack has been consumed.

After the received notification, the patient's BG levels can periodically (e.g. every 30 minutes) be observed. In some embodiments, the BG levels can be observed until two or more successive substantially equal values (e.g. ±20 md/dL) are received.

In some embodiments, if the CIR is accurate and the BG level at the beginning of the test is within the target zone, the BG levels can be observed until two successive normoglycemic values are identified. In that embodiment, the RI time can be selected as the time from insulin administration to the first normoglycemic measurement of successive substantially equal values.

According to the RITA method, the patient can also be asked to avoid additional food intake or insulin delivery during the test. The test may not be carried out during stressed conditions (illness, menses, etc.) because of the increased basal requirements that can alter the accuracy of the RITA results.

In some embodiments, selection of the RI time in an insulin pump can be done by a physician or a user and the insulin boluses can be administered according to the tested RI time. The RI time can be reset automatically without a user interface.

In another embodiment, the insulin delivery device may remind the user to perform the RITA test every predetermined period of time (e.g. six months) since RI time may be changed over time. For example, the insulin delivery device may remind the user to perform the RITA test more frequently if there is a significant variability in the RI time between previous tests.

The RITA method can be implemented in an insulin infusion device (e.g. pump), in a glucose monitoring device, in a remote control and/or in a personal computer. The RITA method can be implemented in a device that can deliver insulin and monitor glucose levels and that can deliver insulin automatically or semi-automatically according to sensed glucose levels (closed, semi closed or open loop system).

The RITA method can also be implemented in an insulin infusion device including insulin dispensing patch unit and a remote control unit, wherein a glucose sensing apparatus (e.g. glucometer) is integrated in the remote control unit. For example, the dispensing patch unit may be composed of two parts: a reusable part that contains all electronic and driving components (i.e. relatively expensive components) and a disposable part that contains insulin reservoir and other inexpensive components. The glucose sensing apparatus (e.g. glucometer) may alternatively be integrated in the reusable part of the infusion patch unit of the device. Preferably, the RITA feature can be implemented in the remote control unit of the insulin infusion device. Alternatively, the RITA feature can be implemented in the reusable part of the dispensing patch unit of the device.

The RITA feature can be implemented in the dispensing patch unit that continuously senses and monitors body glucose concentration levels and can concomitantly deliver insulin into the body. The dispensing patch unit can comprise a reusable part and a disposable part. The insulin dispensing and glucose sensing capabilities can be combined into a semi-closed loop system, where a processor-controller apparatus controls the dispensing of basal insulin according to the sensed glucose concentration. The RITA feature can be implemented in the remote control unit of the device. Alternatively, this capability can be implemented in the reusable part of dispensing patch unit of the device. Alternatively, the RITA feature can be implemented in both the reusable part of the dispensing patch unit of the device and the remote control unit of the device.

FIGS. 3a-d show some embodiments of the device (1000). The device (1000) can be used for dispensing therapeutic fluids (e.g. insulin) to the body of the patient. The device can comprise a dispensing unit (1010), a remote control unit (1008), and a blood glucose (BG) monitor (90). The dispensing unit can be connected to a cannula (6) that can penetrate the skin (5) to deliver insulin to the subcutaneous tissue. The dispensing unit can be composed of one part contained in one housing (1003), as shown in FIGS. 3a-c, or two housings (1001, 1002), comprising a reusable part (1) and a disposable part (2) respectively, as shown in FIG. 3d. Flow programming and data acquisition can be done by a remote control unit (1008) or directly by operating buttons located on the dispensing unit housing (1004). The BG monitor can be contained within the remote control unit or the dispensing unit (not shown).

The RITA feature (10) can be located in the dispensing unit (1010), as in FIG. 3a, the BG monitor (90), as in FIG. 3b or, in the remote control unit (1008), as illustrated in FIGS. 3c-d. The BG monitor can be located, for example, in the remote control unit. The device may include a continuous glucose monitor (CGM) that can be incorporated within the dispensing unit housing or as a stand alone unit (not shown).

FIGS. 4a-b show the device in which the dispensing unit (1010) (a.k.a. the "patch unit" or the "patch") can be adhered to the user's skin (5). The patch unit programming, user inputs and data acquisition can be done, for example, by a remote control unit (1008) or by buttons and screen on the patch unit's housing (not shown).

The patch unit (1010) can be comprised of one housing (1003), as in FIG. 4a, or two housings (1001, 1002), as in FIG. 4b, that are configured as a reusable part (1) and a disposable part (2). The patch unit (1010) can be connected to a cannula (6) that penetrates the skin (5) for delivery of insulin to the body. The patch unit (1010) can be firmly adhered to the user's skin by adhesive means or removable attached to a cradle unit (not shown) as disclosed in our co-owned, co-pending U.S Provisional Patent Application No. 60/876,679.

The RITA feature (10) can be contained in the reusable part (1) of the two part patch unit (1010) (not shown) or in the remote control unit (1008). The remote control includes an input means (3020) and a display (3030) for programming the RITA (10) and the patch unit (1010). FIG. 4c shows the remote control unit (1008) with the input means (3020) and display (3030) in more detail.

Figure 5A:
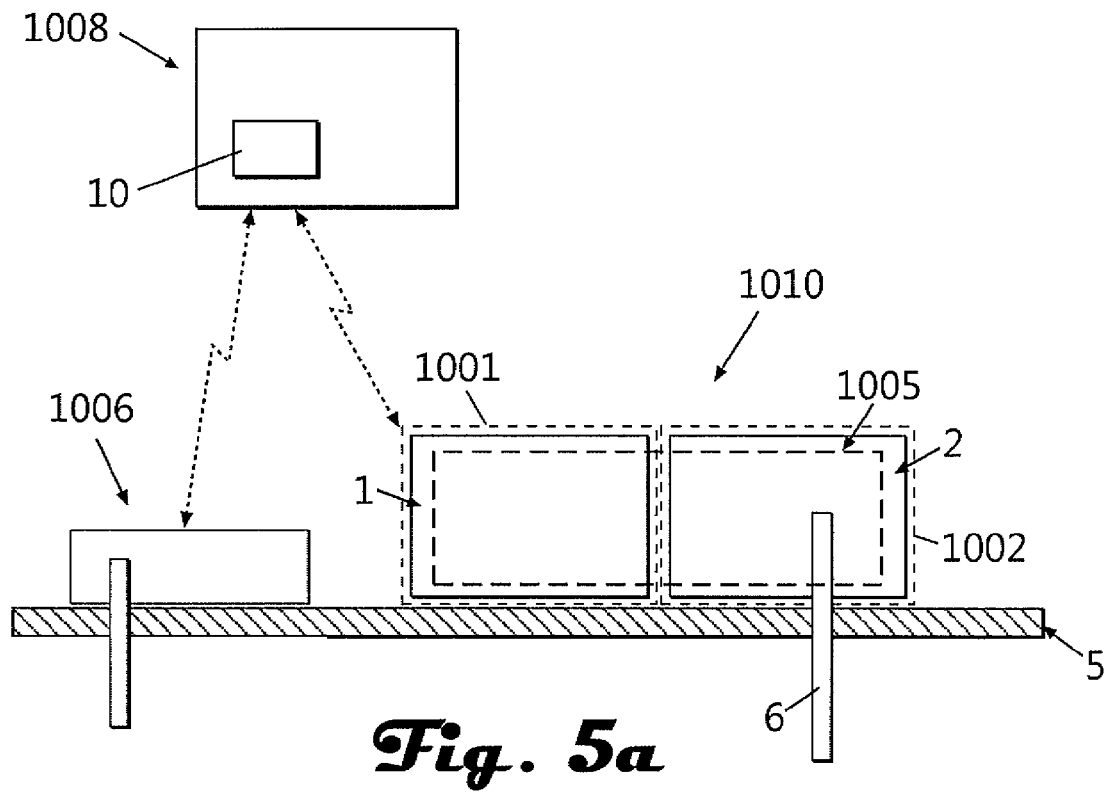
FIGS. 5a-b show the insulin infusion device that includes .a continuous subcutaneous glucose monitor (hereinafter "CGM")
Figure 5B:
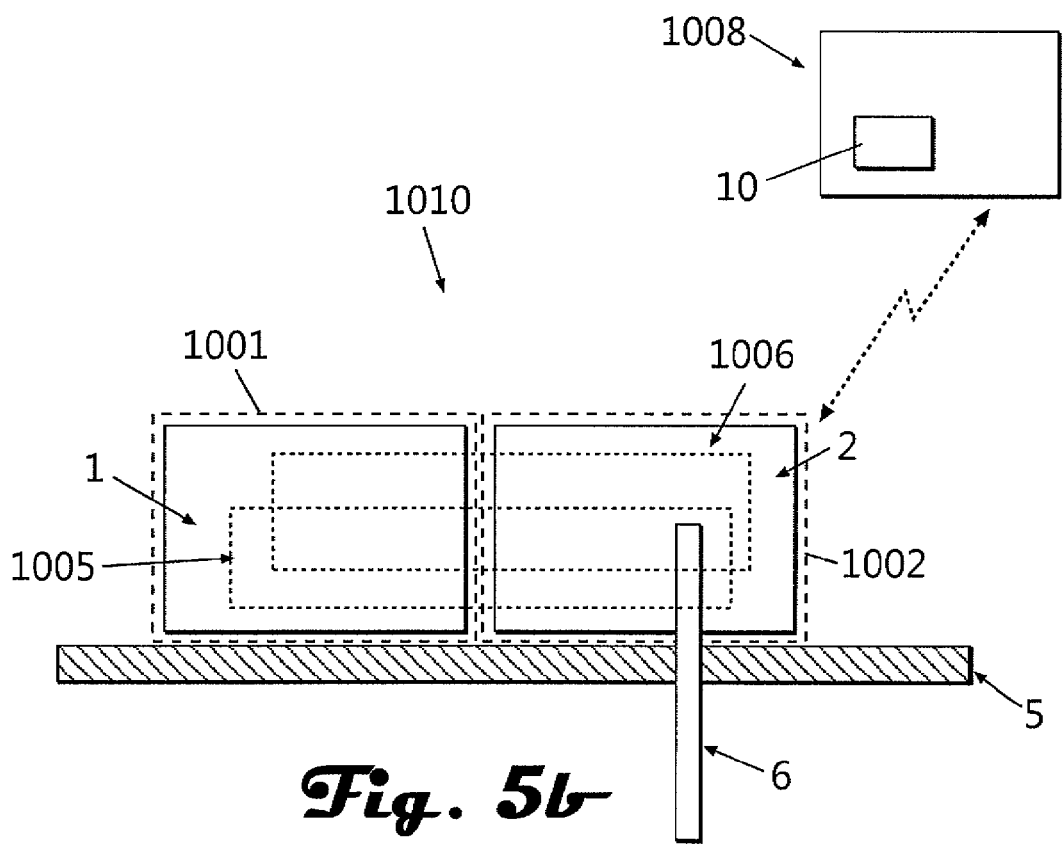

FIGS. 5a-b shows the device that comprises two part patch unit (1010), remote control unit (1008) and continuous glucose monitor (CGM) apparatus (1006). The two part patch unit contains a dispensing apparatus (1005) that can be divided between the reusable part (1) and the disposable part (2). The reusable part (1) can be contained in a housing (1001) and the disposable part (2) can be contained in the housing (1002). The RITA feature (10) can be implemented within the remote control unit (1008) or within the patch unit (not shown).

FIG. 5a shows a stand alone configuration of the CGM apparatus in which continuous glucose readings can be transmitted to the remote control and patch units. FIG. 5b shows the CGM apparatus (1006) which is contained within a two part patch unit and is divided between the reusable part (1) and the disposable part (2). The dispensing apparatus (1005) can be connected to a cannula and the CGM apparatus (1006) can be connected to a separate probe (not shown) or both apparatuses can be connected to a single cannula/probe as described in detail in our previous U.S. application Ser. No. 11/706,606. The CGM can be a separate unit or incorporated within the dispensing unit and the RITA feature can be provided within the remote control unit.

In some embodiments, insulin can be dispensed according to the CGM readings (closed loop system) or according to CGM readings and additional pre-meal bolus inputs (semi-closed loop system). For example, the assessed RI time in the semi-closed loop system can be used for bolus calculation.

Figure 6:
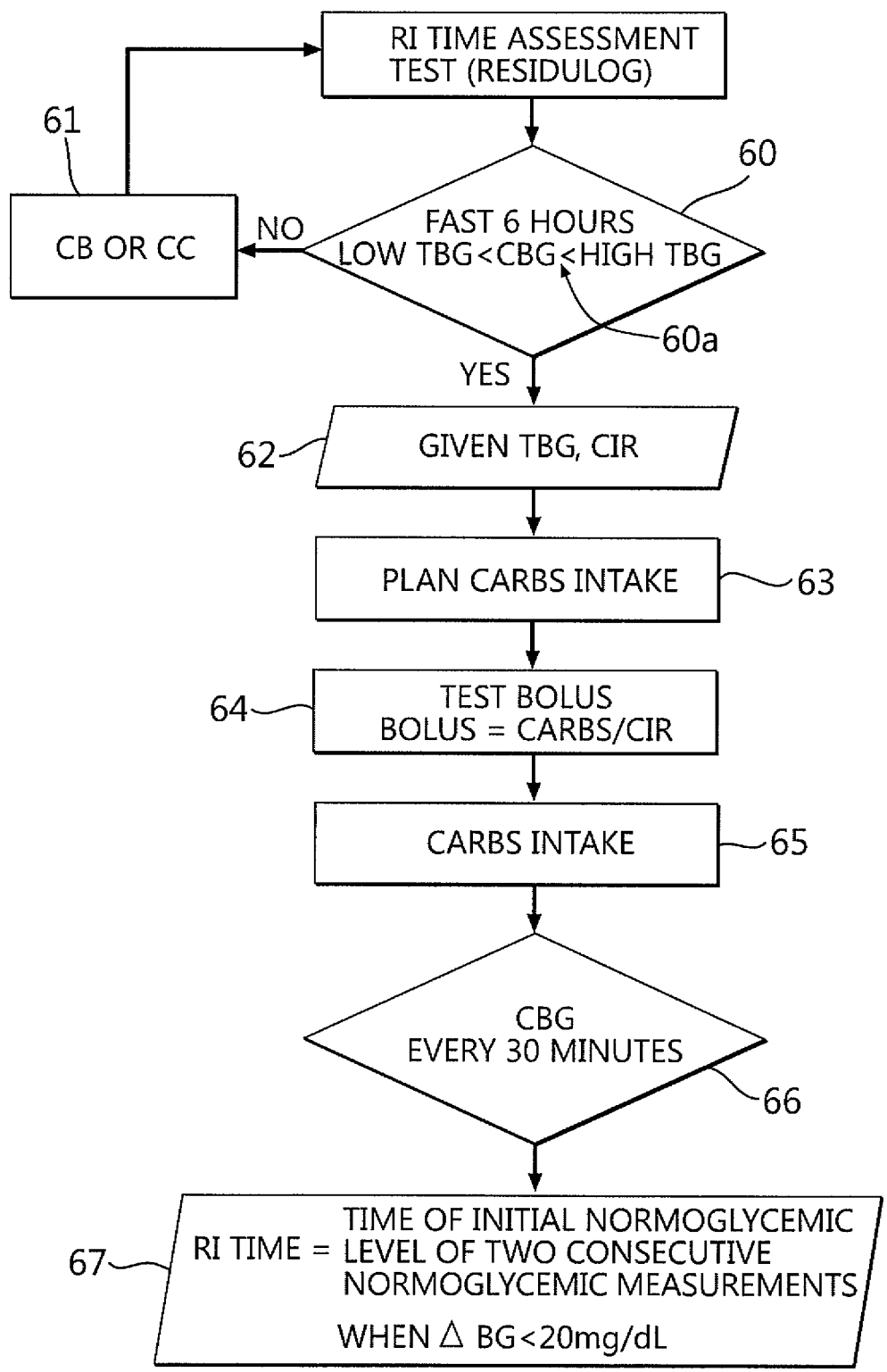
FIG. 6 shows the RITA method block diagram.

FIG. 6 shows a flow chart for assessing RI time value that can be implemented by the RITA feature. At (60), the user may be required to fast for a period of time (e.g., at least 6 hours) and avoid strenuous physical activity prior to the beginning of the test procedure. At (60a), the current blood glucose can also be verified to make sure that the patient is in the normoglycemia state (low target blood glucose (TBG) <CBG<(high target blood glucose (TBG)). At (61), the CBG can be corrected, if necessary, by administering the correction bolus (CB) if CBG>high TBG or by consuming carbs (CC) if BG<low TBG. At (62), pre test parameters (e.g., Target Blood Glucose (TBG) in the range of 80 mg/dL-120 mg/dL and Carbohydrate-to-Insulin Ratio (CIR)) can also be selected.

At (63), a contemplated amount of carbohydrates planned to be consumed by the patient (e.g., the amount of carbohydrates in an energy bar) can be received. At (64), the insulin bolus based on the contemplated carb intake (63) and CIR (62) can be administered. For example the bolus can be calculated according to the following formula: Bolus=Carbs/CIR.

At (65), a confirmation that the patient consumed the contemplated meal (63) can be received. At (66), current BG levels ("CBG") values can be monitored periodically (e.g. every 30 minutes) until 2 or more successive substantially equal values are obtained (e.g. within the range of ±20 md/dL). At (67), the RI time can be selected as the time from insulin administration to the first measurement of successive substantially equal BG values.

In another embodiment, the BG level at the beginning of the test may not be within the target zone. In that case, the successive BG measurements that are substantially equal may not necessarily indicate the normoglycemia range. In addition, the BG at the end of the test is not necessarily equal to the BG level measured prior to insulin administration. For example, if the CIR applied by the user is inaccurate (which directly derives an insulin dose inadequate to compensate for the meal), the plateau may not necessarily be substantially equal to the initial BG measurement (i.e. BG at the beginning of the test).

In another embodiment, at least one additional measurement can be carried out even if two successive substantially equal measurements have been obtained. In that case, if the additional BG measurement is not approximately the same as the previous 2 measurements, then additional measurements can be obtained until 2 or more successive substantially equal values (e.g. ±20 md/dL) are obtained again.

In another embodiment, detection of successive substantially equal measurements may be required during a predefined time period. For example, the RI time can be determined only if successive substantially equal measurements are obtained during a 30 minute time period.

The RITA feature can also utilize a continuous glucose monitor ("CGM"). For example, glucose levels can be measured automatically every few minutes and RI time can be deduced when plateau of the glucose vs. time curve occurs. In some embodiments, the CGM may alarm the patient of any CBG value deviations from the target zone during the test.

Figure 7A:
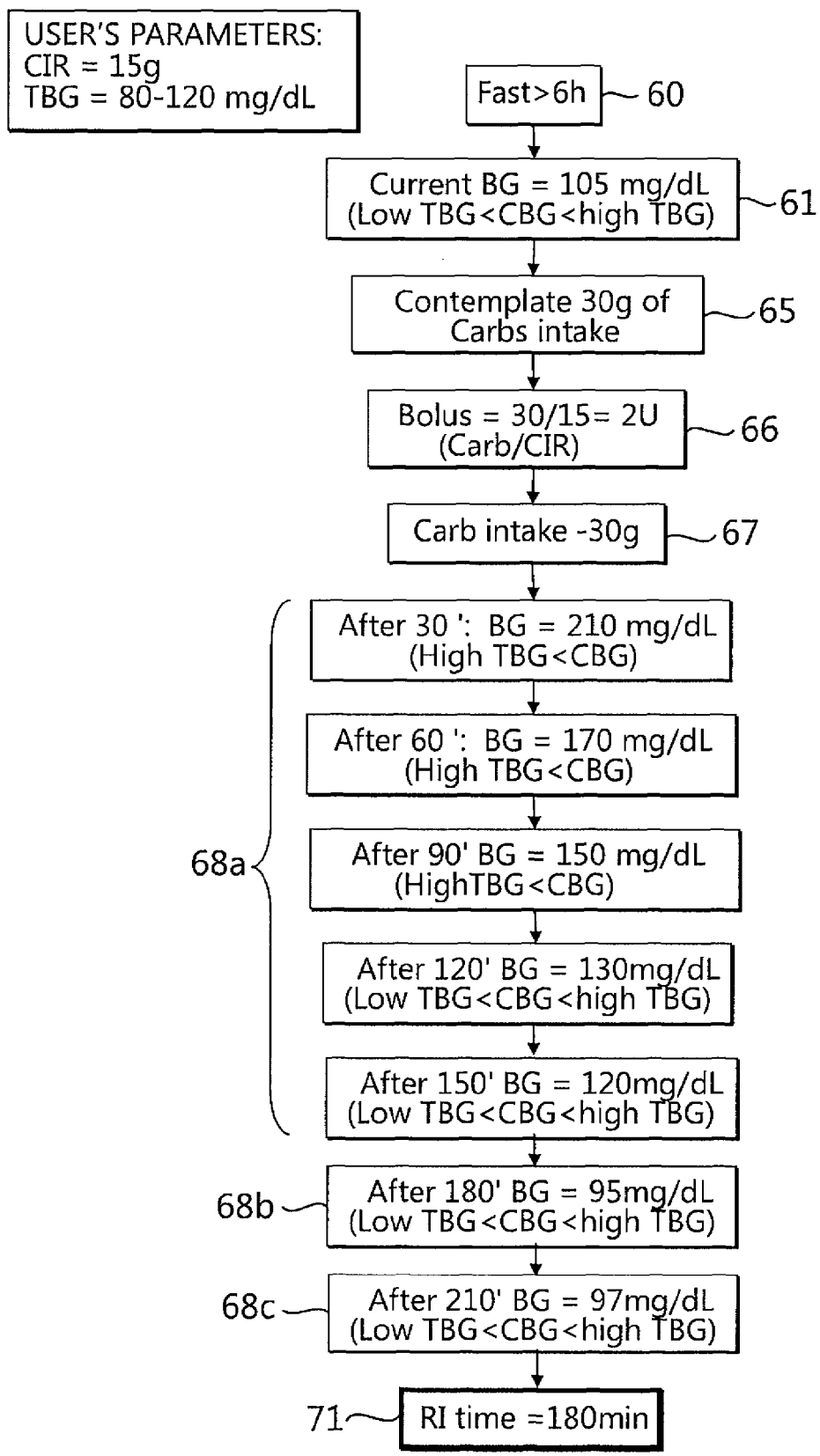
FIGS. 7a-b show numerical example of the RITA method and a glucose level as related to the time curve.

FIG. 7a illustrates one example of a method for assessing RI time. For the purposes of this example, the following values have been selected: CIR=15 grams; TBG range=80-120 mg/dL. At (60), the patient is asked to fasts for at rest six hours. At (61), the Fasting BG is measured to be 105 mg/dL (within the TBG range). At (65), it is determined that the patient contemplates to consume an energy bar, which has 30 grams of carbohydrates. At (66), an insulin bolus of 2U is administered corresponding to the contemplated carbohydrate intake. At 67, the patient consumes the energy bar. At (68), the patient's blood glucose (BG) is monitored every 30 minutes until normoglycemia is reached for at least two consecutive measurements with a difference of no more than 20 mg/dL.

In the example presented on FIG. 7a, two consecutive substantially equal measurements are detected after 150 minutes. However, the first of the two consecutive measurements was above the normoglycemia range. Consequently, the third consecutive measurement at (68b) was taken. In this example, an additional measurement is performed 30 minutes after the third measurement. At (68c), the result of the additional measurement is substantially equal (e.g.<±20 mg/dL). Consequently at (71), the RI time is determined to be 180 minutes corresponding to the first of the two consecutive substantially equal measurements within the TBG range.

Figure 7B:
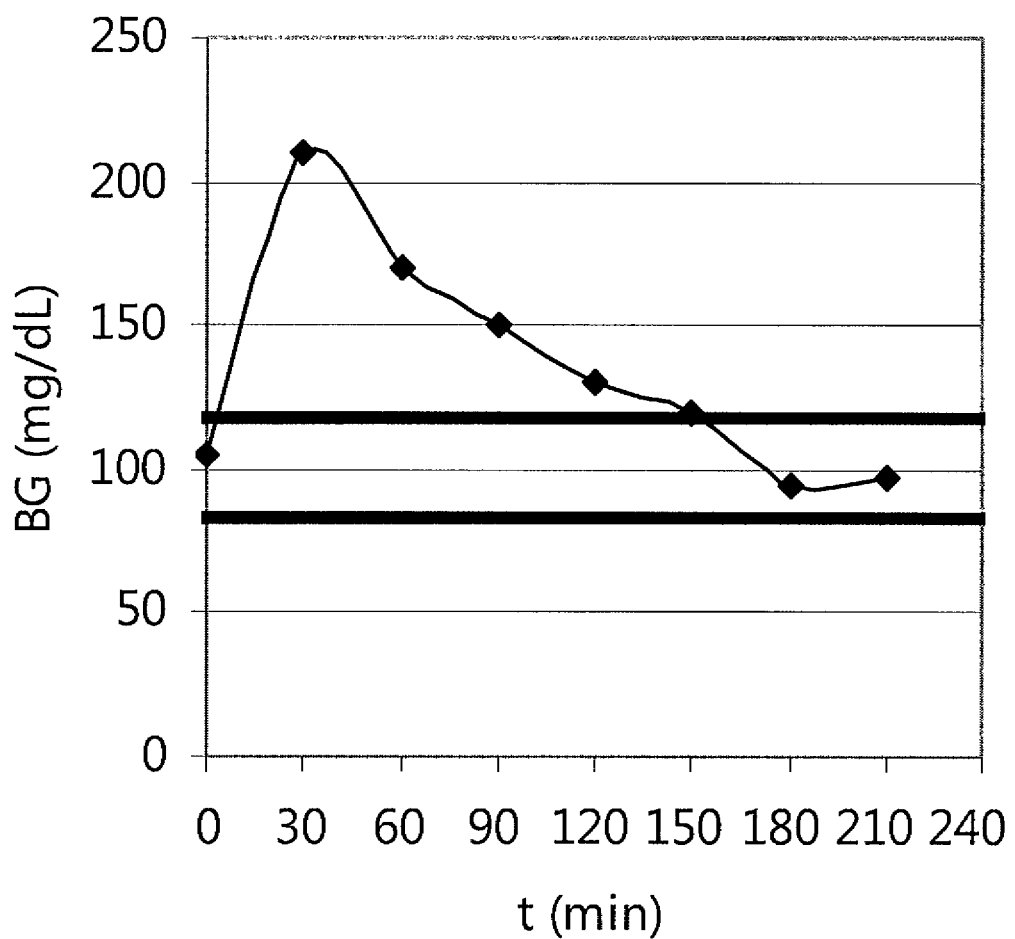

FIG. 7b illustrates an exemplary plot corresponding to patient's observed BG values in example presented on FIG. 7a. Two horizontal gray lines on that plot represent the boundaries of the target zone associated with a particular patient (80 mg/dL<BG<120 mg/dL). In some embodiments, the boundary lines can be tailored to meet specific patient's needs. In some embodiments, the CGM apparatus can be used for more frequent BG measurements (e.g., every 5 minutes).

Figure 8A:
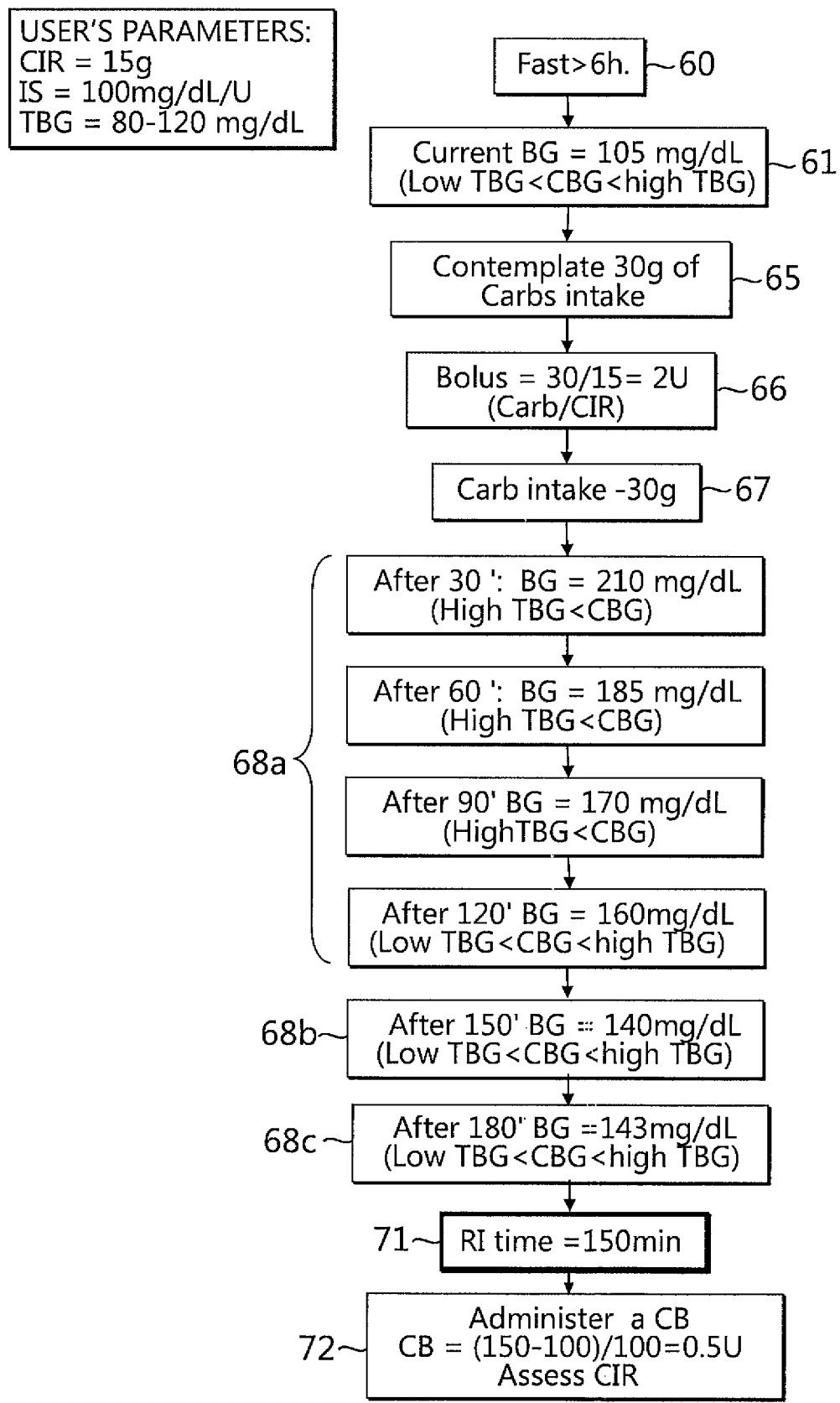
FIGS. 8a-b show another numerical example of the RITA method and a glucose level as related to the time curve.

FIG. 8a illustrates another flow chart representing an exemplary method of assessing the RI time. According to this method, the initial parameters are determined as follows: CIR =15 grams; IS=100 mg/dL/U; TBG range=80-120 mg/dL. At (60), the patient is asked to fasts at least for six hours. At (61), the fasting BG is determined to be 105 mg/dL (within the TBG range). At (65), it is determined that the patient contemplates to consume a snack bar which has 30 grams of carbohydrates. For example, this determination can be made based on information provided by the user. At (66), an insulin bolus of 2U is administered corresponding to the contemplated carbohydrate intake. At (67), the patient consumes the snack bar. At (68), the blood glucose (BG) is monitored every 30 minutes until at least two consecutive measurements with a difference of no more than 20 mg/dL are obtained. In this example, normoglycemia is not achieved, however a plateau is reached within 150 minutes (step 68b). An additional measurement 30 minutes later remains substantially equal (e.g. <±20 mg/dL) (step 68c). Consequently, at (71), the RI time is assessed.

In the example presented above, the plateau was reached while the user's blood glucose remained above the desired target range (80-120 mg/dL). Consequently, at (72), a correction bolus is administered based on the user's insulin sensitivity. The user can also be urged to reassess his/her CIR. Assessment can be done according to a method disclosed in our co-owned, co-pending U.S Provisional Patent Application No. 60/936,690. In some embodiments, if the plateau is reached while the user's blood glucose level remains below the desired blood glucose range (TBG), the user can be advised to consume more carbohydrates and/or reassess his/her CIR.

Figure 8B:
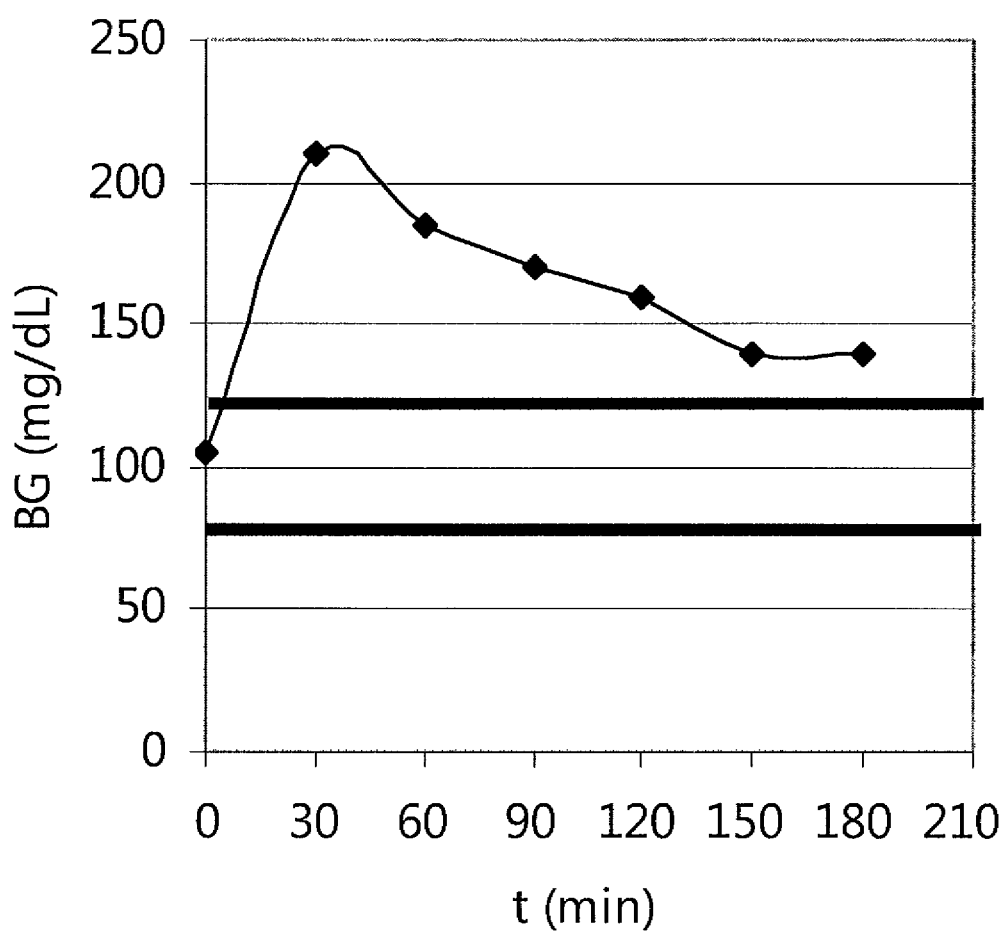

FIG. 8b is an exemplary plot that illustrates patient's observed BG values over time. In the beginning when t=0, the patient consumes the above referenced carbs load. The two horizontal gray lines represent the target zone's boundaries associated with a particular patient (80 mg/dL<BG<120 mg/dL). It can be seen that the user does not reach the target zone and remains hyperglycemic after the BG has reached a plateau.

Figure 9A:
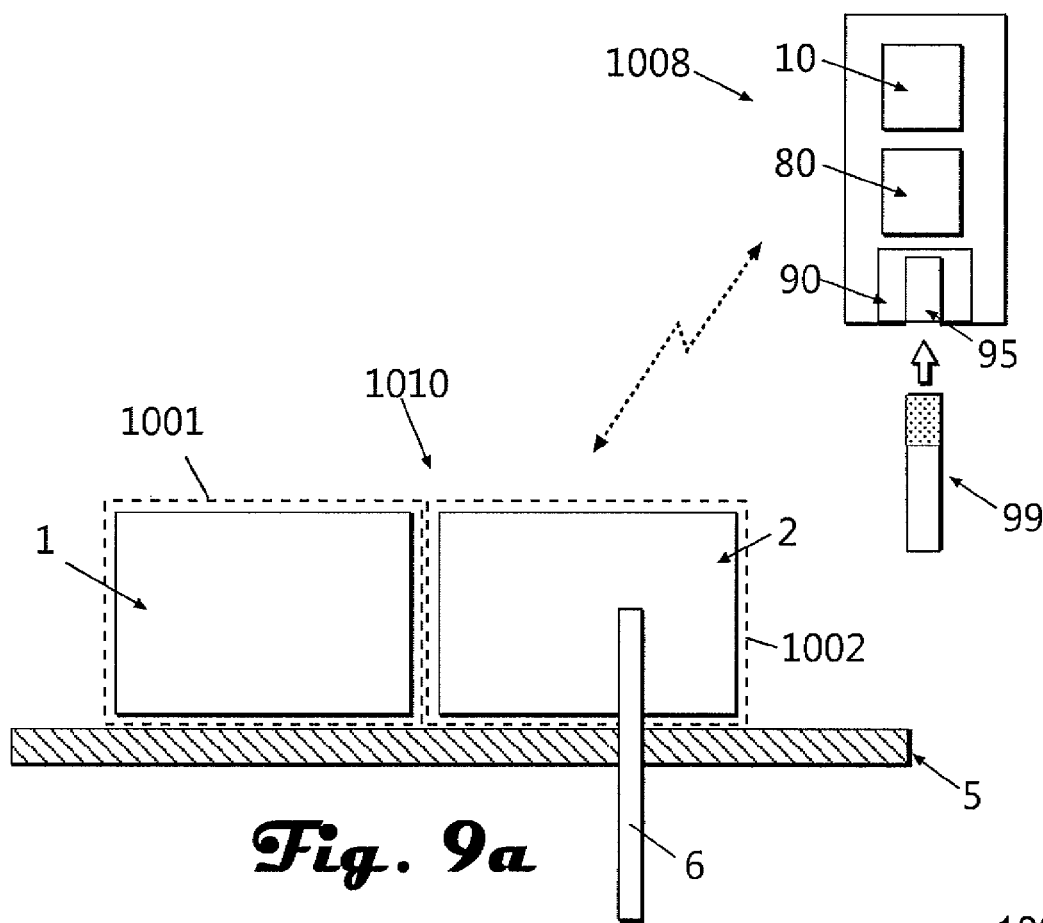
FIGS. 9a-c show the insulin infusion device that includes blood glucose monitor in the remote control unit, the dispensing unit or as a stand alone unit, wherein the RITA feature is provided within the remote control unit.
Figure 9B:
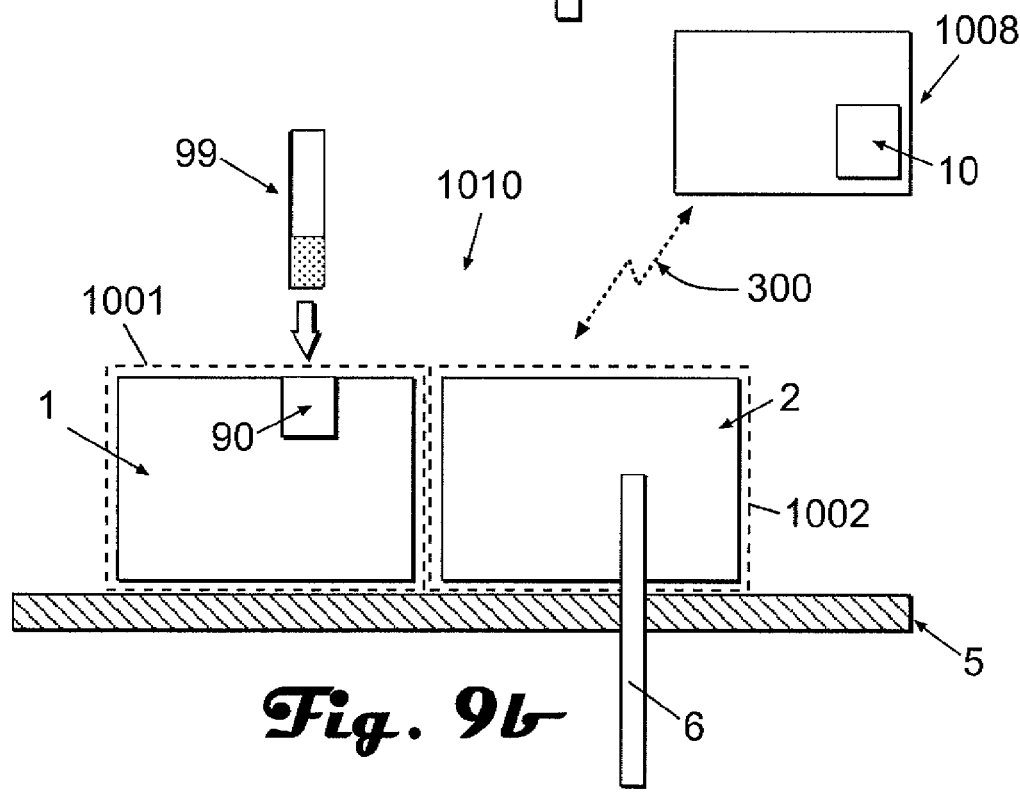
Figure 9C:
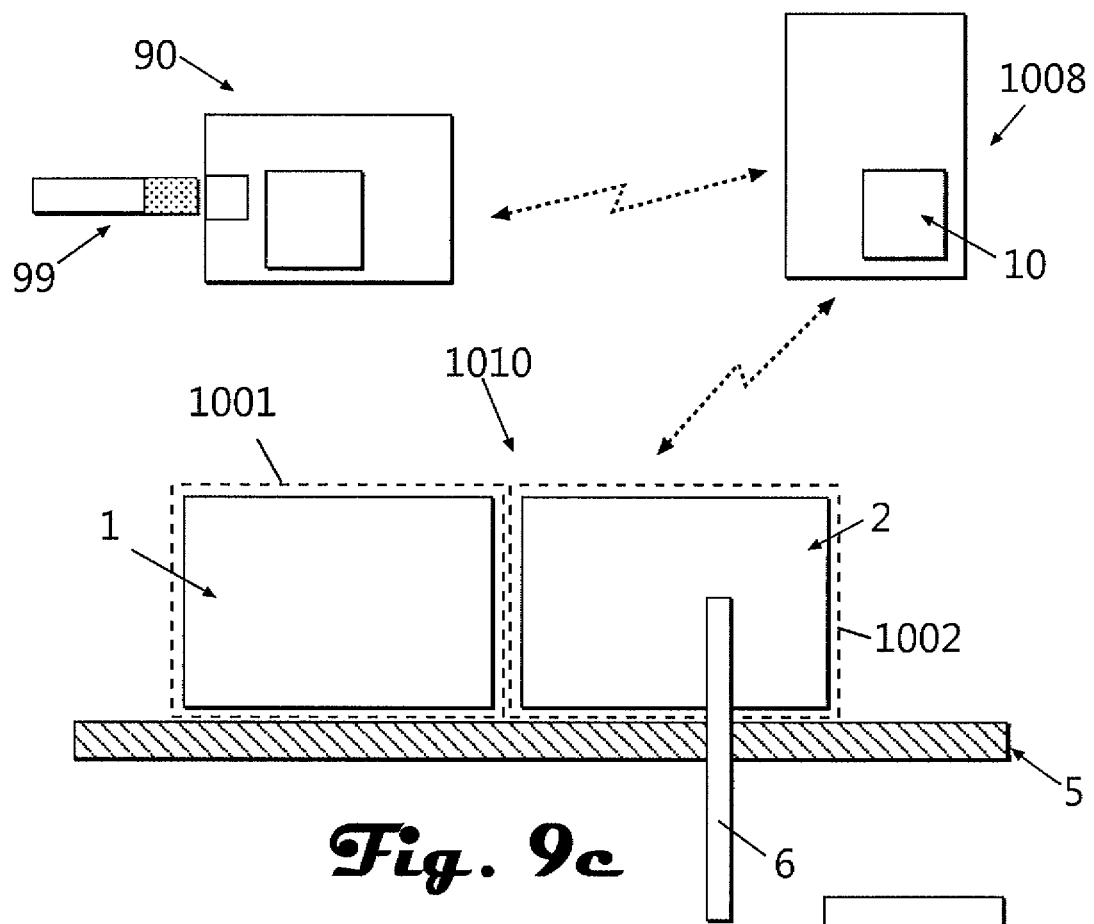
Figure 10A:
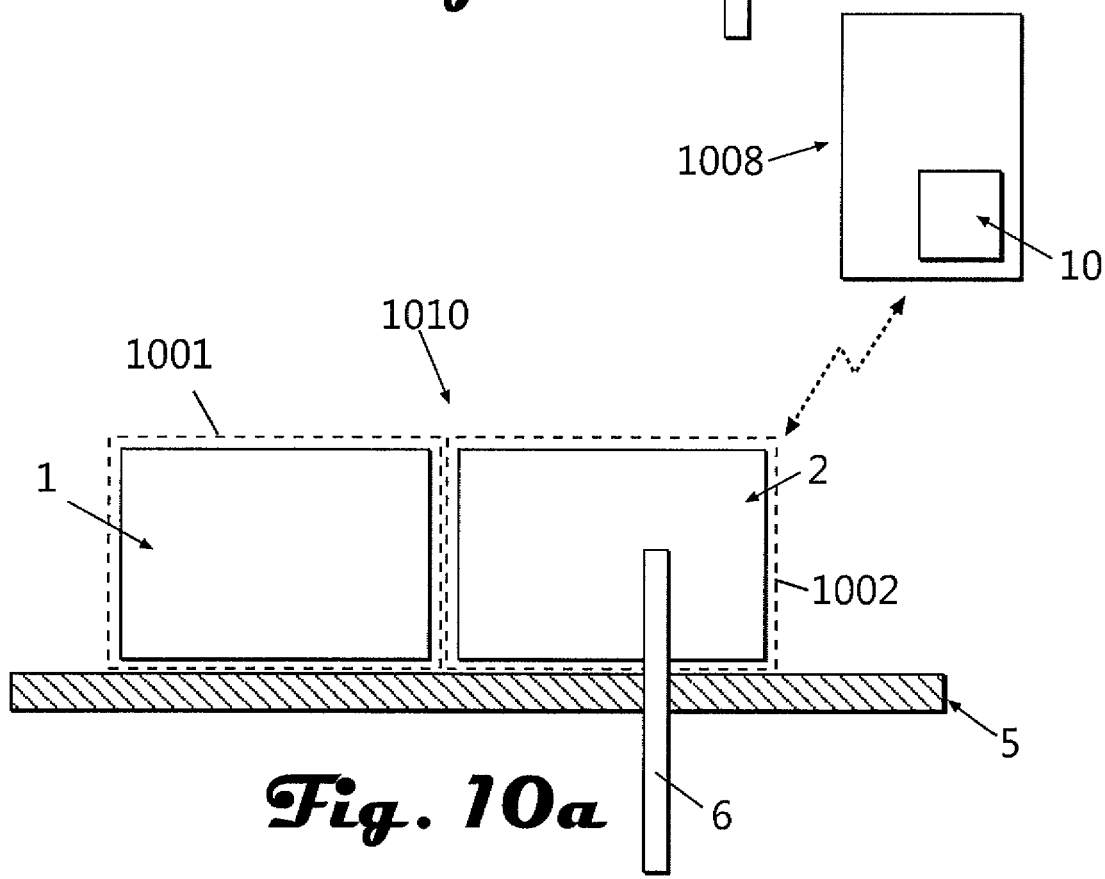
FIGS. 10a-b show the insulin infusion device that includes blood glucose monitor, where the RITA is provided .within the remote control unit and the dispensing unit.
Figure 10B:
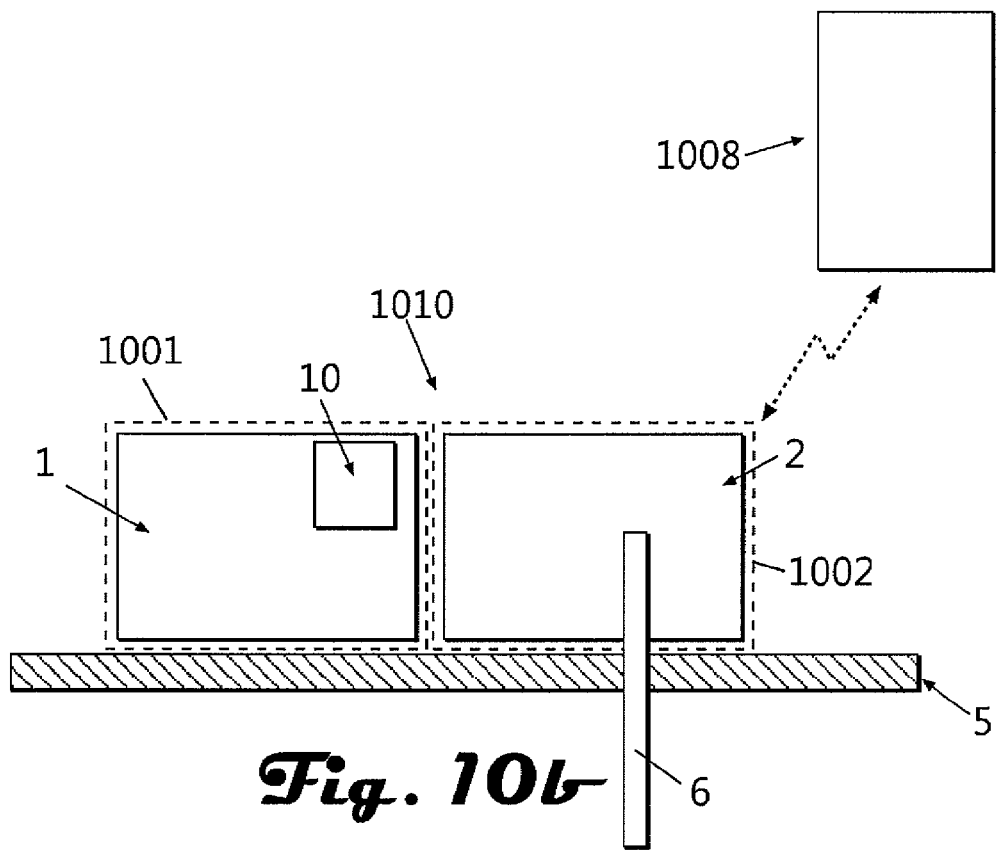

FIGS. 9a-c show various locations of blood glucose (BG) monitor (90) for acquiring blood glucose (BG) readings to be used by the RITA feature (10). Specifically, FIG. 9a shows a BG monitor (90) located in the remote control unit (1008). The BG monitor (90) can include an opening (95) for insertion of the test strip (99). The patient can extract blood from the body, place a blood drop on the test strip (99) and insert the test strip into the opening (95). The glucose readings can be displayed on the screen (80) of the remote control unit (1008). FIG. 9b illustrates a BG monitor (90) located in the reusable part (1) of the patch unit (1010). A communication channel (300) can be configured to connect the BG monitor (90) residing in the patch unit (1010) and the RITA feature (10) residing in the remote control unit (1008). FIG. 9c illustrates an exemplary embodiment in which glucose readings are (90) received from a stand alone BG monitor. FIGS. 10a-b show various locations of the RITA feature (10). In FIG. 10a the RITA feature (10) is located in the remote control unit (1008). In FIG. 10b the RITA feature (10) is located in the reusable part (1) of the patch unit (1010).

Figure 11:
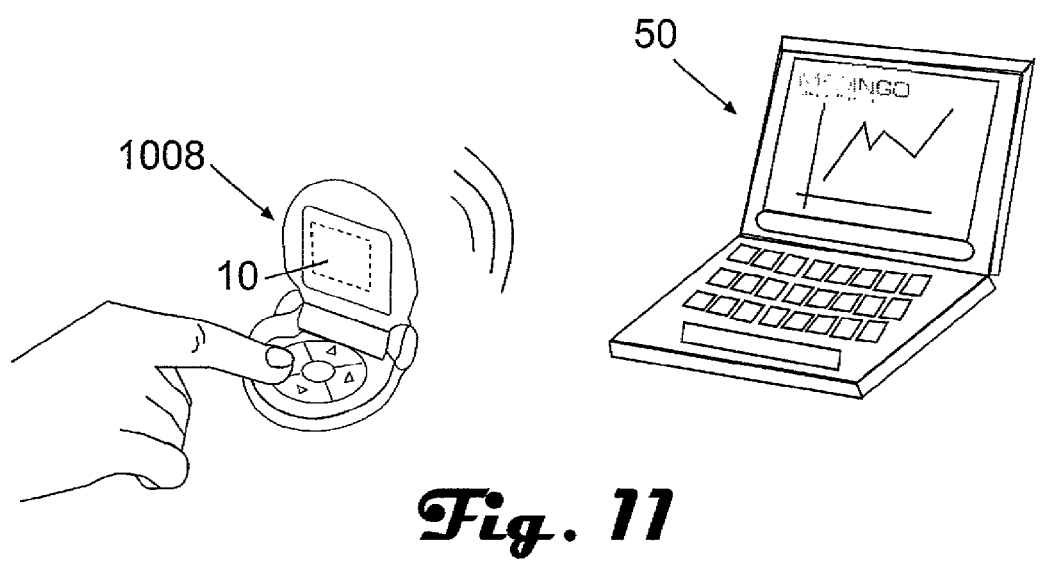
FIG. 11 shows data downloading from the RITA feature to a PC.

FIG. 11 shows embodiment of the RITA feature (10) which is located in a remote control unit (1008) that communicates with an external PC (50). According to this embodiment, any patient specific parameters changes (e.g., RI time) can be saved using a PC and may be displayed in any graphical or non-graphical manner. In some embodiments, the saved data can be automatically delivered to any caregiver (by electronic mail or any other means) for evaluation, validation, or clinical intervention.

Any and all patents, applications, articles and/or publications referenced in this specification are hereby incorporated by reference herein in their entireties.

Although particular embodiments have been disclosed herein in detail, this has been done by way of example for purposes of illustration. only, and is not intended to be limiting with respect to the scope of the appended claims, which follow. Other embodiments, advantages, and modifications are considered to be within the scope of the following claims.

What is claimed is:

1. A method for assessing a residual insulin time of a patient comprising:
   receiving a confirmation that an insulin dose has been administered to a the patient, the insulin dose corresponding to an amount of carbohydrates consumed by the patient;
   repetitively receiving a value corresponding to the patient's blood glucose level;
   identifying at least two consecutively received values based on a predetermined criteria; and
   assessing a residual insulin time corresponding to a time period between receipt of the confirmation and the identification of the at least two consecutively received values.

2. The method of claim 1, wherein the predetermined criteria is based on a target blood glucose range.

3. The method of claim 2, wherein the two consecutive values are identified only if both consecutive values are within the target blood glucose range.

4. The method of claim 1, wherein the predetermined criteria is based on an initial blood glucose level measured prior to the administration of the insulin dose.

5. The method of claim 1, wherein the predetermined criteria is based on a difference between the at least two consecutively received values.

6. The method of claim 5, wherein the difference is less than 20 mg/dL.

7. The method of claim 1, wherein the insulin dose is administered to the patient subsequently to a confirmation that the patient's blood glucose level is within a target blood glucose range.

8. The method of claim 1, wherein the time corresponding to the identification of the at least two consecutively received values is the time when the first of the two identified values was received.

9. The method of claim 1, further comprising advising the patient to bring the patient's blood glucose level within a target blood glucose range prior to consuming the carbohydrates.

10. The method of claim 1, further comprising advising the patient to abstain from food for an abstention period of time prior to consuming the carbohydrates and administering the insulin dose.

11. The method of claim 1, wherein the value corresponding to the patient's blood glucose level is repetitively received with a predetermined frequency.

12. The method of claim 1, wherein the predetermined criteria is based on a third consecutively received value corresponding to the patient's blood glucose level.

13. The method of claim 12, wherein the at least two consecutively received values are identified if the difference between the third consecutive value and the first consecutive value is less than a predefined threshold.

14. The method of claim 1, further comprising initiating an administration of a correction bolus if the two identified consecutively received values are above the target blood glucose range.

15. The method of claim 14, wherein the initiation of the administration of the correction bolus is performed by notifying the patient.

16. The method of claim 14, wherein the initiation of the administration of the correction bolus is performed by activating a pump.

17. The method of claim 1, further comprising advising the patient to assess a carbohydrate-to-insulin ratio (CIR) value if the deviation between one of the at least two consecutively received values and the patient's blood glucose level measured prior to the insulin administration exceeds a predefined threshold.

18. The method of claim 1, further comprising advising the patient to consume more carbohydrates if the two identified consecutively received values are below a target blood glucose range.

19. The method of claim 1, wherein the patient's blood glucose level is received from a continuous glucose monitor (CGM).

20. A medical device comprising:
   a tangible machine-readable storage medium embodying instructions that when performed by one or more processors result in operations comprising:
      receiving a confirmation that an insulin dose has been administered to the patient, the insulin dose corresponding to an amount of carbohydrates consumed by the patient;
      repetitively receiving a value corresponding to the patient's blood glucose level;
      identifying at least two consecutively received values based on a predetermined criteria; and
      assessing a residual insulin time corresponding to a time period between receipt of the confirmation and the identification of the at least two consecutively received values.

21. The device of claim 20, wherein the predetermined criteria is based on a difference between the at least two consecutively received values.

22. A medical device comprising:
a continuous glucose monitor (CGM); and
a tangible machine-readable storage medium embodying instructions that when performed by one or more processors result in operations comprising:
receiving a confirmation that an insulin dose has been administered to the patient, the insulin dose corresponding to an amount of carbohydrates consumed by the patient;
repetitively receiving a value corresponding to the patient's blood glucose level from the continuous glucose monitor (CGM);
identifying at least two consecutively received values based on a predetermined criteria; and
assessing a residual insulin time corresponding to a time period between receipt of the confirmation and the identification of the at least two consecutively received values.

\* \* \* \* \*